(12) United States Patent
Broad et al.

(10) Patent No.: US 8,938,051 B2
(45) Date of Patent: Jan. 20, 2015

(54) MULTI-LEAF COLLIMATORS

(75) Inventors: Martin Broad, Bromley (GB); Mark Alexander Furth, Crawley (GB); Duncan Neil Bourne, Redhill (GB); Ryan David Wightwick, Crawley (GB)

(73) Assignee: Elekta AB (publ), Stockholm (SE)

( * ) Notice: Subject to any disclaimer, the term of this patent is extended or adjusted under 35 U.S.C. 154(b) by 135 days.

(21) Appl. No.: 12/882,667

(22) Filed: Sep. 15, 2010

(65) Prior Publication Data

US 2011/0026683 A1 Feb. 3, 2011

Related U.S. Application Data

(63) Continuation-in-part of application No. 12/423,909, filed on Apr. 15, 2009, now abandoned, and a continuation-in-part of application No. PCT/EP2008/003183, filed on Apr. 21, 2008.

(51) Int. Cl.
*A61B 6/06* (2006.01)
*A61N 5/10* (2006.01)
*G21K 1/04* (2006.01)

(52) U.S. Cl.
CPC ............... *A61N 5/1042* (2013.01); *G21K 1/04* (2013.01); *G21K 1/046* (2013.01)
USPC .......................................... 378/152; 378/147

(58) Field of Classification Search
CPC ...................................................... G21K 1/046
USPC ........................................................ 378/152
See application file for complete search history.

(56) References Cited

U.S. PATENT DOCUMENTS

| 4,868,844 | A | * | 9/1989 | Nunan | 378/152 |
| 5,012,506 | A | * | 4/1991 | Span et al. | 378/152 |
| 2008/0073591 | A1 | * | 3/2008 | Mohr | 250/494.1 |
| 2008/0165930 | A1 | * | 7/2008 | Perkins | 378/152 |
| 2008/0292058 | A1 | * | 11/2008 | Nagata | 378/152 |

FOREIGN PATENT DOCUMENTS

| CN | 1819856 A | 8/2006 |
| EP | 0 193 509 A | 9/1986 |
| EP | 0 257 989 A | 3/1988 |

(Continued)

OTHER PUBLICATIONS

Office Action for U.S. Appl. No. 12/423,909, filed Apr. 15, 2009, Mailed on Jun. 30, 2010.

(Continued)

*Primary Examiner* — Hoon Song
(74) *Attorney, Agent, or Firm* — Westman, Champlin & Koehler, P.A.; Z. Peter Sawicki; Amanda Prose

(57) ABSTRACT

A multi-leaf collimator for a radiotherapy apparatus comprises at least one array of laterally-spaced elongate leaves, each leaf being driven by an associated motor connected to the leaf via a drive means so as to extend or retract the leaf in its longitudinal direction, the drive means comprising a sub-frame on which at least a subset of the motors are mounted, the sub-frame being mounted at a location spaced from the leaf array in a direction transverse to the lateral and longitudinal directions, and including a plurality of threaded drives disposed longitudinally, each being driven by a motor and being operatively connected to a leaf thereby to drive that leaf.

28 Claims, 5 Drawing Sheets

(56) References Cited

FOREIGN PATENT DOCUMENTS

| | | | |
|---|---|---|---|
| EP | 0257989 | A1 | 3/1988 |
| JP | 2003210595 | A | 7/2003 |
| JP | 2008206563 | A | 9/2008 |
| WO | 9641349 | A1 | 12/1996 |
| WO | 2007124248 | A | 11/2007 |

OTHER PUBLICATIONS

Japanese Office Action; 2011-505364; Oct. 2, 2012.
Chinese Office Action; CN Application No. 200880129924.4; Apr. 25, 2013.

* cited by examiner

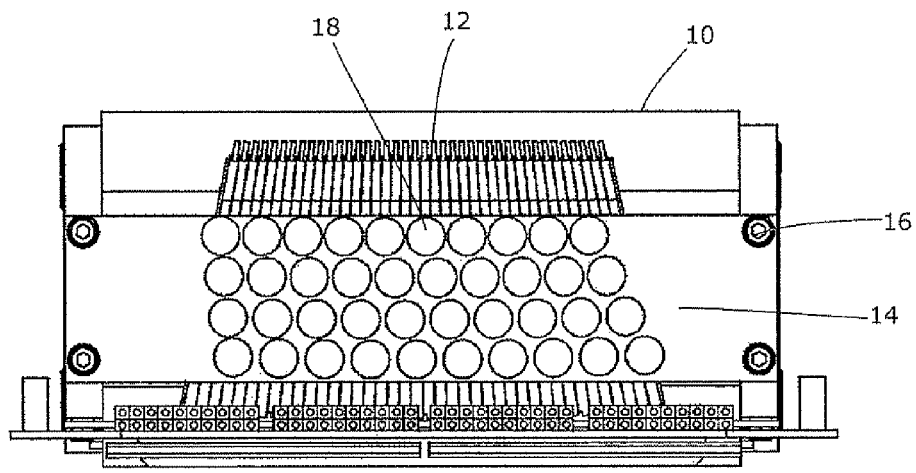
Fig 1 - Prior Art
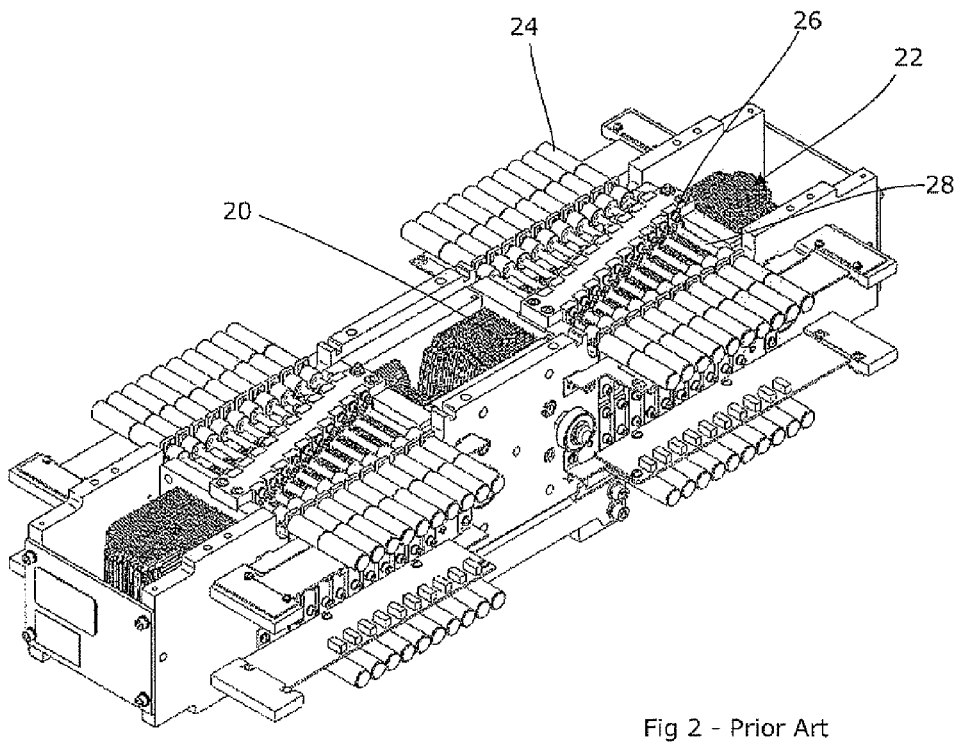
Fig 2 - Prior Art

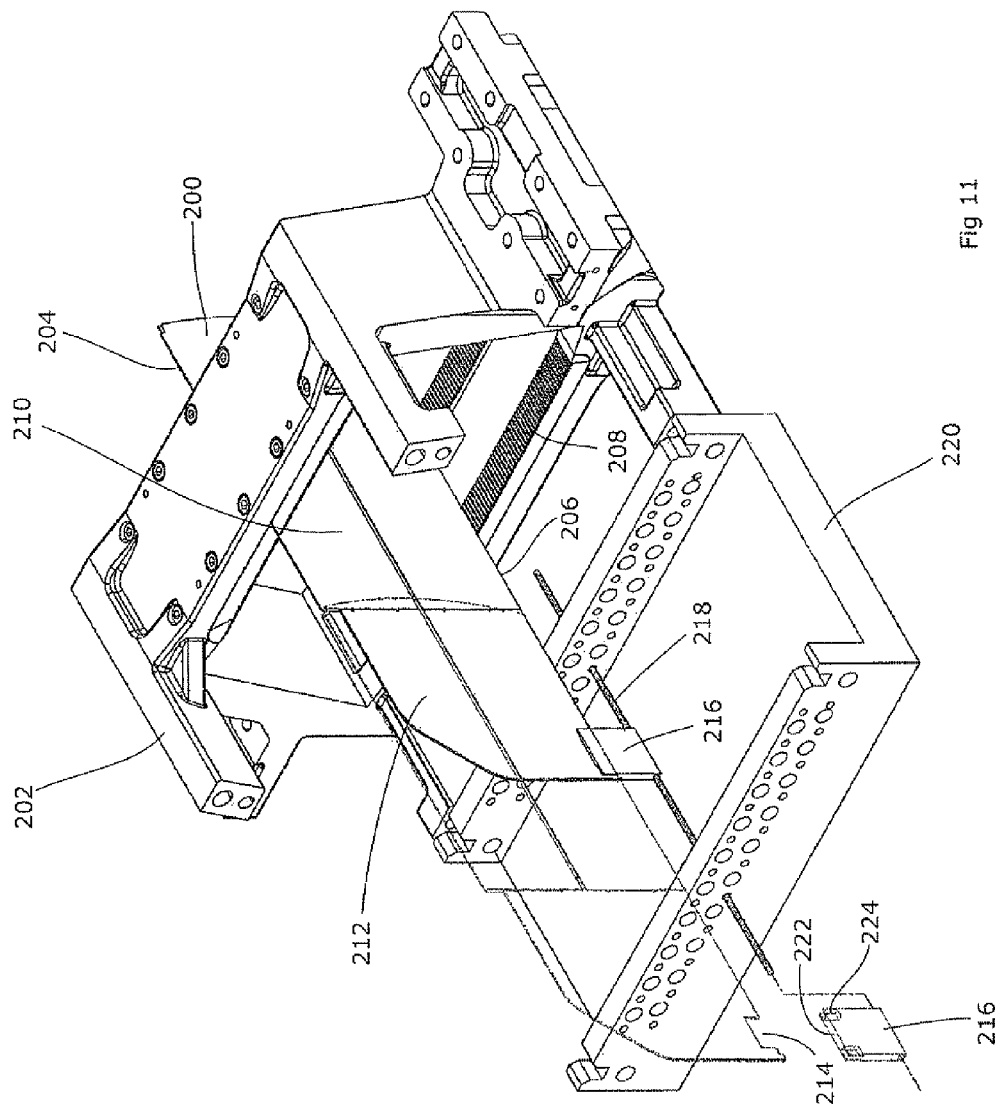

1

MULTI-LEAF COLLIMATORS

CROSS-REFERENCE TO RELATED APPLICATION

The present application is a Continuation-in-Part of and claims priority of U.S. patent application Ser. No. 12/423,909, filed Apr. 15, 2009, which is a Continuation-in-Part and claims priority of International Application No. PCT/EP2008/003183, filed Apr. 21, 2008, the content of which is hereby incorporated by reference in its entirety.

FIELD OF THE INVENTION

The present invention relates to multi-leaf collimators.

BACKGROUND ART

Radiotherapeutic apparatus involves the production of a beam of ionising radiation, usually x-rays or a beam of electrons or other sub-atomic particles. This is directed towards a cancerous region of the patient, and adversely affects the tumour cells causing an alleviation of the patient's symptoms. Generally, it is preferred to delimit the radiation beam so that the dose is maximised in the tumour cells and minimised in healthy cells of the patient, as this improves the efficiency of treatment and reduces the side effects suffered by a patient, A variety of methods of doing so have evolved.

One principal component in delimiting the radiation dose is the so-called "multi-leaf collimator" (MLC). This is a collimator which consists of a large number of elongate thin leaves arranged side to side in an array. Each leaf is moveable longitudinally so that its tip can be extended into or withdrawn from the radiation field. The array of leaf tips can thus be positioned so as to define a variable edge to the collimator. All the leaves can be withdrawn to open the radiation field, or all the leaves can be extended so as to close it down. Alternatively, some leaves can be withdrawn and some extended so as to define any desired shape, within operational limits. A multi-leaf collimator usually consists of two banks of such arrays, each bank projecting into the radiation field from opposite sides of the collimator.

The leaves on the MLC leaf bank need to be driven in some way. Typically, this is by a series of lead screws connected to geared electric motors. The leaves are fitted with a small captive nut in which the lead screws fit, and the electric motors are fixed on a mounting plate directly behind the leaves. Rotation of the leadscrew by the motor therefore creates a linear movement of the leaf. The leaf drive motors are inevitably wider than a single leaf thickness, so in order to be able to drive each leaf the motors have to be mounted in a particular pattern as shown in FIG. 1. This shows a housing 10 for an array of adjacent MLC leaves 12. Behind the array, a motor mount 14 is fixed in place to housing 10 via bolts 16 so that it lies behind the leaves 12. A motor 18 for each leaf 12 is fixed to the motor mount 14.

Each motor 18 is generally tubular and from one end (as shown in FIG. 1) therefore appears circular. The motors are wider than an individual leaf and are therefore arranged in a staggered pattern. In this example, the motors 18 are arranged in four offset rows so that the centre of a motor is aligned with each leaf. As a result of this, the leadscrew nuts therefore have to be fixed to the leaves in one of a variety of positions, meaning that (in this case) four different leaf shapes need to be manufactured.

In an alternative system referred to as the "Beam Modulator" and shown generally in FIG. 2, leaves are driven by a rack and pinion system. A gear rack 20 is machined into the top or bottom of the leaves 22 and is driven by motors 24 fixed to the side of the leaf bank. The motor gear pinions 26 are mounted to an extension shaft 28 of a suitable length to enable the drive to be carried across to the appropriate leaf to be actuated.

In our earlier patent application GB-A-2423909, we describe a modular design similar to the Beam Modulator drive system. The application describes a design where a system of miniature gears and racks are incorporated into a detachable module. The linear motion is transmitted to the leaf via a slotted feature in the rack and engages in a leaf drive coupling fitted to the rear of the leaf.

The choice of drive system is influenced by the quantity and thickness of the leaves in the leaf bank. For example, the MLC leaf bank has 40 leaves per side and has an average leaf thickness of 3.6 mm. This thickness and number of leaves allows for a conventional solution of placing the motors directly behind the leaves and actuating them via a leadscrew which passes through the centre of the leaf.

The diameter of the leadscrew in this design is limited to 2.5 mm, as this is largest diameter that can pass into the leaf without interfering with neighbouring leaves. Conveniently, it is also a standard ISO thread size. The leadscrew has to drive a leaf weighing around 800 g, and at certain head/gantry angles the full weight of the leaf is suspended by the thread alone. Due to the small engagement area of the thread, the leadscrew therefore experiences high frictional loads and requires regular lubrication to maintain an acceptable service life. The performance of the leadscrew is also adversely affected by a whipping motion that can arise when the leaf nut is close to the motor, in which the long free end of the leadscrew can oscillate as it rotates. In addition, the leadscrew experiences a buckling load when the leaf is pushed to the far end of the leadscrew. There is also a certain degree of noise due to this motion of the leadscrew.

The Beam Modulator design employs a thinner leaf in order to increase the resolution of the leafbank. This leaf thickness of only 1.75 mm influences the selection of the drive system. A lead screw system as used on the MLC would not be a viable solution as it would require a 1.5 mm diameter leadscrew; as the leaf travel is longer, the leadscrew would suffer increased whipping and buckling. Leadscrews with a high aspect ratio are also extremely difficult and costly to manufacture and are likely to fracture if they are not adequately supported. In addition, the number of motors required (40 per side) could not be fitted in behind the leaves due to their size.

The drive system for Beam Modulator therefore incorporates a rack and pinion system, with the motors disposed on either side, top and bottom of the leaf bank. The motors are fixed to the side of the leaf bank, and pinions are driven from the motors on extension shafts requiring 10 different lengths, in addition a staggered bearing block is incorporated in which the extension shafts runs. 8 such bearing blocks are required for the leaf bank.

Because the motors are dispersed along the 4 sides of the leaf bank, the bank has to be removed for motor servicing. Removal of the leaf bank is a lengthy process, and problems can occur with radiation performance if the leaf bank is not replaced in the same position.

The rack is machined into the top or bottom of the tungsten leaf; the bearing surface that would be positioned at the top of the leaf therefore has to be offset in order to make way for the rack. This has the undesired effect of reducing the shielding effect of the leaf, as some 8 mm is lost off the top/bottom of the leaf for the rack and bearing surface.

In order for smooth operation of the rack a certain amount of clearance has to be maintained between the rack and pinion. Each of the 80 motors therefore has to be checked when assembling the leaf bank. This clearance can vary leaf to leaf, depending on manufacturing tolerances, and can lead to unwanted backlash once the pinion and motor gearbox begin to wear. Such backlash will affect the positional accuracy of the leaves.

GB-A-2423909 describes a removable module which alleviates many of the service issues problems experienced with the beam modulator. However, as it incorporates a rack and pinion system it will suffer from backlash in the same way. The MLC Rack and Pinion System was originally designed around a 160 leaf MLC, but limitations in available space in the treatment head above and below the leafbank as well as restrictions on the overall head diameter create problems for fitting this type of Actuator. The gear racks in the actuator are positioned to match the leaf pitch; during operation the racks extend into the radiation beam, which may have effects on beam performance—particularly if there is an error in the pitching. The Actuator module also contains a high part count, including many precision cut gears and racks making this expensive to produce.

Thus, the leaf thickness/pitch and motor size affects the method in which the actuation is carried to the leaf, and once a suitable method is derived (of the 2 practical drive solutions, leadscrew and rack and pinion) the design can have inherent problems with wear, noise, production and assembly costs, backlash and servicing issues.

SUMMARY OF THE INVENTION

The present invention therefore seeks to provide a compact MLC actuator, that addresses many of the problems associated with a conventional leadscrew system, with the potential to drive a greater number of leaves without relying on a complex drive design and a high part count (relative to the number of leaves). This has the benefit of reducing production costs and assembly times. The drive mechanism should ideally not reduce the shielding effect of the tungsten leaves or interfere with the radiation beam. A modular design would also improve servicing issues by allowing the complete removal of the drive system from the leafbank.

The MLC actuator of the present invention is designed for use on a 160 leaf MLC, but can of course be applied to MLCs with a lesser or greater number of leaves. The drive will ideally be capable of moving the leaves faster than previous MLCs to offer better dynamic treatment therapies, and will be useable for MLCs with smaller width and/or pitch of the leaves of, say, 1.5 mm as compared to the 10 mm diameter of the drive motors even within a limited overall head height.

The width above the leaves (i.e. on the source side) is generally smaller than that below the leaves, due to the tapered design of the leafbank. Therefore, any design should ideally encompass this difference in leaf width and available space without complicating the design and increasing the required numbers of component parts.

The present invention therefore provides a multi-leaf collimator for a radiotherapy apparatus, comprising at least one array of laterally-spaced elongate leaves, each leaf being driven by an associated motor connected to the leaf via a drive means so as to extend or retract the leaf in its longitudinal direction, the drive means comprising a sub-frame on which at least a subset of the motors are mounted, the sub-frame being mounted at a location spaced from the leaf array in a direction transverse to the lateral and longitudinal directions, and including a plurality of threaded drives disposed longitudinally, each being driven by a motor and being operatively connected to a leaf thereby to drive that leaf.

The threaded drives will typically be leadscrews, but other arrangements such as a ballscrew can be used.

Mounting the drive motors in this way allows them to be distributed more space-efficiently, and allows the drive system to be modular, without requiring rack and pinion gears.

To take advantage of the ability to distribute the motors in a more space-efficient manner, we therefore prefer that a plurality of the motors mounted on the subframe are mounted at a first longitudinal end, and the remainder of the motors mounted on the subframe are mounted at a second, opposing, longitudinal end. Those leadscrews not at an edge of the array are preferably neighboured on either lateral side by one leadscrew driven by a motor mounted at the same longitudinal end and a second leadscrew driven by a motor mounted at the opposite longitudinal end. This results in the motors being arranged in pairs with a gap between which provides space for mounting the motors. The pairs of motors can be arranged one above the other to allow the necessary clearances, meaning that the leadscrews will be mounted in the subframe at one of two spacings from the leaf, with laterally neighbouring leadscrews being mounted at alternating spacings. The leadscrews can be mounted within a bore in the subframe.

Still greater space efficiency can be achieved by including a lower subframe, mounted at a location spaced from the leaf array in an opposite direction to that of the upper array and on which the remainder of the motors are mounted. This can be designed in a generally similar manner to that of the (upper) subframe, except as regards the leaf pitch which will need to be adjusted as a result of the varying inclination of the leaves. We prefer that half of the leaves are driven from the subframe and half are driven from the lower subframe. Adjacent leaves in the array can be driven alternately from the subframe and from the lower subframe.

The leaves are preferably mounted in a machined guide thereby to allow longitudinal motion. The subframe(s) can be mounted on the guide.

In this way, drive can be supplied to the leaves from an elongate edge thereof. This drive can be transmitted to the substantially radio-opaque leaves via a drive coupling attached to the rear of each leaf. This can be located outside the radiation beam and can therefore be of a lightweight non-radio-opaque material.

The drive means can further include a threaded member on the leadscrew. This is preferably restrained from rotation around the leadscrew by the remainder of the operative connection between it and the leaf. One way of doing so is for the threaded member to urge a laterally extending lug, thereby to connect to the drive coupling. The lug can engage with a recess on the drive coupling, and can include laterally-spaced flanges positioned to lie adjacent the drive coupling to prevent rotation of the lug around the threaded member. The lug ideally has a reasonable length in a direction parallel to the threaded member, to prevent rotation around axes transverse to the threaded member. A length that is at least 50% of its length transverse to the threaded member will typically suffice.

The lug can alternatively be held in a machined slot in the subframe; that slot can be machined with non-parallel sides to assist in guiding the lug in the light of the offset nature of the load that it needs to carry.

If desired, a collimator can be provided with 160 leaves, for future expansion, but operated as an 80 leaf collimator for compatibility purposes, by grouping adjacent leaves (such as in pairs), each leaf of a group being identically oriented and driven in unison by the same drive means.

BRIEF DESCRIPTION OF THE DRAWINGS

An embodiment of the present invention will now be described by way of example, with reference to the accompanying figures in which;

FIG. 1 shows a view along the leaf direction of a known MLC drive arrangement;

FIG. 2 shows a perspective view of a known beam modulator;

FIG. 11 illustrates an alternative embodiment.

DETAILED DESCRIPTION OF THE EMBODIMENTS

Figure 3:
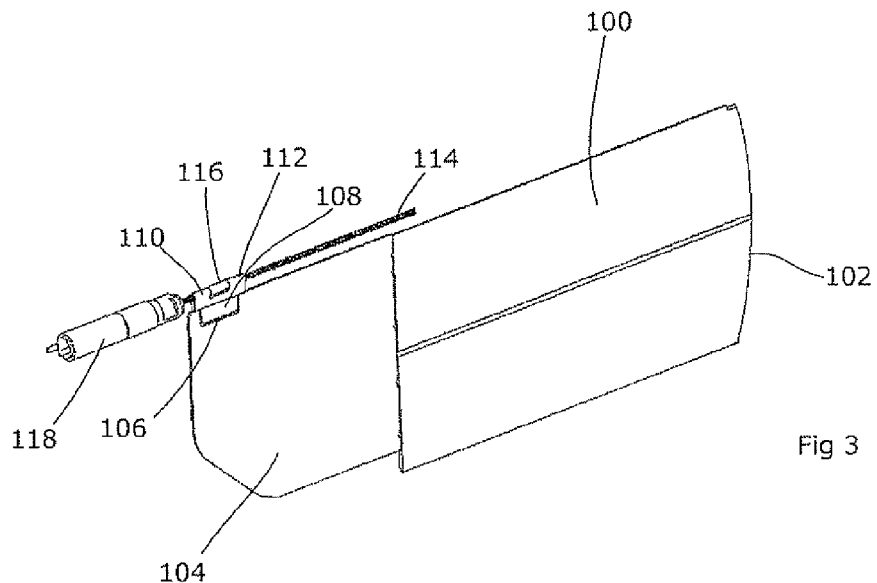
FIG. 3 shows a single leaf according to the present invention.

The inherent limitation on the minimum length of the rack and pinion-type system is the number of motors mounted on the side of the module. For example, assuming that each module is designed to drive 40 leaves, that each motor is 10 mm in diameter and (therefore) spaced 14 mm apart in a double row, then the length of the module will have to be 14×(40/2), i.e. 280 mm, plus the distance over which the leaves are expected to travel. If we take a rough figure of 70 mm for this distance, this makes an overall length for the system of 350 mm. The minimum overall height will be the motor diameter plus the height of the rack, i.e. about 32 mm. A rack and pinion module when mounted on the leafbank will therefore increase the treatment head diameter significantly.

The MLC actuator described herein features a lead screw that runs parallel to the leaf, which means that the length of the drive modules are shorter overall, as the leadscrew only needs to be a slightly longer than the required leaf travel. The overall length of actuator including motors can therefore be about 200 mm, with a height of about 24 mm.

This however faces the difficulty noted above, i.e. that the leadscrew needs a minimum diameter in order to be economic to produce and sufficiently rigid in operation. For MLC arrays in which the individual leaf thickness falls close to or below this diameter, this raises difficulties in accommodating both the leadscrews and the motors that drive them.

The MLC actuator described herein incorporates a leadscrew drive assembly which actuates the leaf indirectly via a lug which projects out from the drive assembly and engages with a drive coupling for the leaf. The leadscrews and lugs run in machined guide slots in a bearing block which both houses the lugs (etc) and provides mounting for the drive assemblies.

It still remains, of course, that the leadscrews may be wider than the leaves, and it will usually be the case that the motors are wider. Accordingly, each leaf will (generally) only be a fraction of the width of its associated drive mechanism. An alternative way of viewing this is that laterally arrayed drive mechanisms will only be able to drive a fraction of the leaves. Therefore, a number of such arrays can drive all of the leaves, if the drive from each array can be transmitted to the leaves satisfactorily. A specific pattern of drive mechanisms is therefore needed in order to mount the leadscrews drives into a compact removable module.

We have chosen to divide the drive to the leaves in a number of ways so as to distribute the drive mechanism arrays. First, leaves can be driven from their upper edge or their lower edge. This is defined by the convention that MLC arrays are usually described as having a top that is closest to the radiation source and a bottom that is closest to the patient. Such a convention is necessary since the MLC array is mounted in a radiation head that rotates around the patient, and therefore in use the array may take up any orientation. Thus, an upper subframe can carry half of the drive mechanisms and drive every other leaf, and a lower subframe can carry the other half to drive the remaining leaves. Next, each subframe can carry two rows of leadscrews, one above the other. The lugs associated with each leadscrew can be of a corresponding length. This spaces the motors and allows them to drive laterally adjacent leadscrews. Finally, the leadscrews do of course have two ends and can be driven from either. Accordingly, half the leadscrews in each subframe can be driven from the front (which we define as the end most distant from the beam) and half from the rear (defined correspondingly). These three binary divisions allow $2^3$ combinations, i.e. each situationally identical drive means drives one in eight leaves. This division can be as follows:

| Leaf | Subframe | Row | Bank |
|---|---|---|---|
| 1* | Lower | bottom | front |
| 2 | Upper | top | front |
| 3 | Lower | top | front |
| 4 | Upper | bottom | front |
| 5 | Lower | bottom | rear |
| 6 | Upper | top | rear |
| 7 | Lower | top | rear |
| 8 | Upper | bottom | rear |
| 9* | Lower | bottom | front |
| 10 | Upper | top | front |
| 11 | Lower | top | front |
| 12 | Upper | bottom | front |
| 13 | Lower | bottom | rear |
| 14 | Upper | top | rear |
| 15 | Lower | top | rear |
| 16 | Upper | bottom | rear |
| 17* | Lower | bottom | front |
| 18 | Upper | top | front |
| 19 | Lower | top | front |
| 20 | Upper | bottom | front |
| 21 | Lower | bottom | rear |
| 22 | Upper | top | rear |
| 23 | Lower | top | rear |
| 24 | Upper | bottom | rear |
| 25* | Lower | bottom | front |
| 26 | Upper | top | front |
| 27 | Lower | top | front |
| 28 | Upper | bottom | front |
| 29 | Lower | bottom | rear |
| 30 | Upper | top | rear |
| 31 | Lower | top | rear |
| 32 | Upper | bottom | rear |

The precise pattern of the leadscrews, lugs, and guiding slots in the bearing block is derived from the angle and pitch of the leaf and the required space for the drive motor. Such a pattern can also allow the drive motor axis to match the leaf centre line, ensuring an efficient transfer of linear motion.

By mounting the drive motors on the front and rear surfaces of the drive modules (upper and lower subframes) the area required to mount the drive motors can be dispersed over 2 faces. This also has the advantage of only requiring 2 sizes of drive mechanism, thereby maintaining a low parts count. Thus, the drive system is split into 2 modules; 2 per side, upper and lower. Each of these modules contains 40 motor/leadscrew drives, allowing for 80 leaves in total. Each module has 20 motors mounted on the front face and 20 on the rear face. The method for mounting of the motor/leadscrew drives is designed specifically to fit the pattern of machined slots in the modules.

This leadscrew design incorporates a precision machined leadscrew with an Acme thread form. The leadscrew nut is injection moulded in a low friction plastic material, which allows the assembly to run quietly without lubrication. The leadscrew nut fits into the lug, and can be easily replaced by removing the motor assembly.

The machined guide slots for the lugs can also be formed with non-parallel sides, and the lugs profiled correspondingly. Thus, viewed along the guide slot, the profile can be akin to that of a key for a cylinder lock. This provides non-vertical surfaces which act as bearings, removing from the leadscrew nut the side and moment loads which will occur in moving the mass of the tungsten leaf. On previous designs, these loads adversely affected the life of the nut. The leadscrew is also supported in this way, reducing both whipping and buckling tendencies. The guide slot profile may also feature a "V" or fir tree shape in the leg of the slot, which will increase the bearing surface area of the key and reduce friction.

A lower portion of the lugs are exposed below the drive module. These sections engage into the top or bottom of a drive coupling for the leaf via a mating cut-out in the drive coupling.

Referring to FIG. 3, this shows a single leaf and its associated drive. The tungsten attenuation portion 100 is relatively thin in a lateral direction in order to allow good resolution, is long in its longitudinal direction to allow a wide range of movement, and is deep in the beam direction to allow good attenuation of the beam. A front edge 102 of the attenuation portion 100 is curved in a generally known manner so as to provide a sharper penumbra. A rear edge of the attenuation portion 100 is vertical, and is joined to a drive coupling 104.

The drive coupling 104 has one edge, in this case the upper edge, which is co-linear with the corresponding edge of the attenuation portion 100 except for a recess 106 into which a lug 108 fits snugly. The opposing edge of the drive portion 104 is rebated back from the corresponding edge of the attenuation portion 100 in order to reduce the overall weight of the device and to avoid interference with the drive mechanism on the other side. It will be apparent that the relative orientations of the attenuation and drive portions can be reversed to allow the leaf to be driven from the top edge (as shown) or from the bottom edge.

The lug 108 fits snugly in the recess 106 of the drive coupling 104 but is not fixed in place. The lug 108 is however attached to a pair of cylinders 110, 112 through which a leadscrew 114 passes, and between which a leadscrew nut 116 is fixed. Thus, as the leadscrew 114 is rotated, the nut 116 is forced in one direction or another and takes with it the cylinders 110, 112, the lug 108, the drive coupling 104 and the attenuation portion 100. The cylinders offer rigidity to the structure retaining the leadscrew nut 116, and also offer lateral support to the leadscrew 144 to inhibit both whipping and buckling.

Finally, at one end of the leadscrew 114, a motor 118 is provided in order to drive the leadscrew.

Thus, by simple reversal of the orientations of the drive coupling 104 and/or the motor 118/leadscrew 114, two of the above divisions can be achieved. The remaining third division is achieved by substitution of a longer lug 108. Accordingly, the spatial distribution of the various drive motors is achieved with an exceptionally low parts count.

Figure 4:
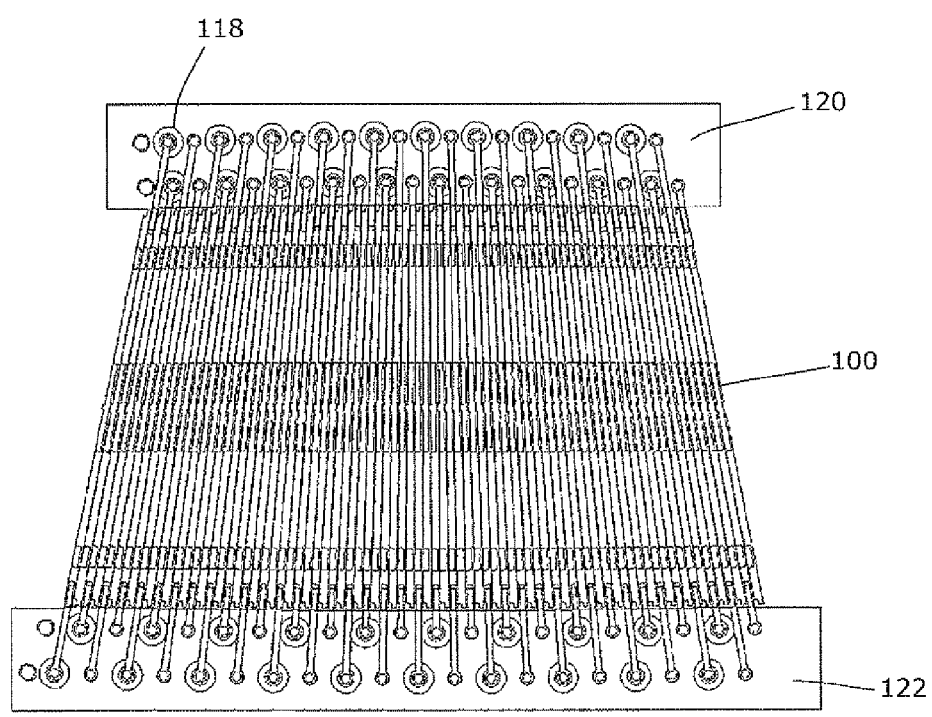
FIG. 4 shows a view of the leaf drive according to the present invention, along the direction of a leaf.

FIG. 4 shows one leaf bank from one end. The side-by side (i.e. laterally arrayed) leaves 100 are supported at their top and bottom edges in a leaf guide (not visible). Counting the leaves from the left hand side of FIG. 4, the odd-numbered leaves are driven from their lower edge and the even-numbered leaves are driven from their upper edge. Thus, an upper subframe 120 carries leadscrews, lugs, motors etc for the even-numbered leaves and a lower subframe 122 carries leadscrews, lugs, motors etc for the odd-numbered leaves. Apart from dimensional issues relating to the divergent nature of the leaves 100, the two subframes are functionally and structurally identical.

Within each subframe, for example the upper subframe 120, the first two leaves that are controlled (i.e. leaves 2 and 4) are connected via lugs 108 of varying lengths to a leadscrew running in a guide machined in the otherwise solid block that forms the subframe. These two guides are placed at differing heights so as to separate the motors 118.

The next leaf (i.e. leaf 6) is then connected to a leadscrew at the same upper level as leaf 2. To provide sufficient space, the motor for leaf 6 is located at the other end of the subframe 120 and drives its associated leadscrew from its other end. The pattern then continues, so that the next leaf that is driven in a manner identical to leaf 2 is leaf 10.

Figure 5:
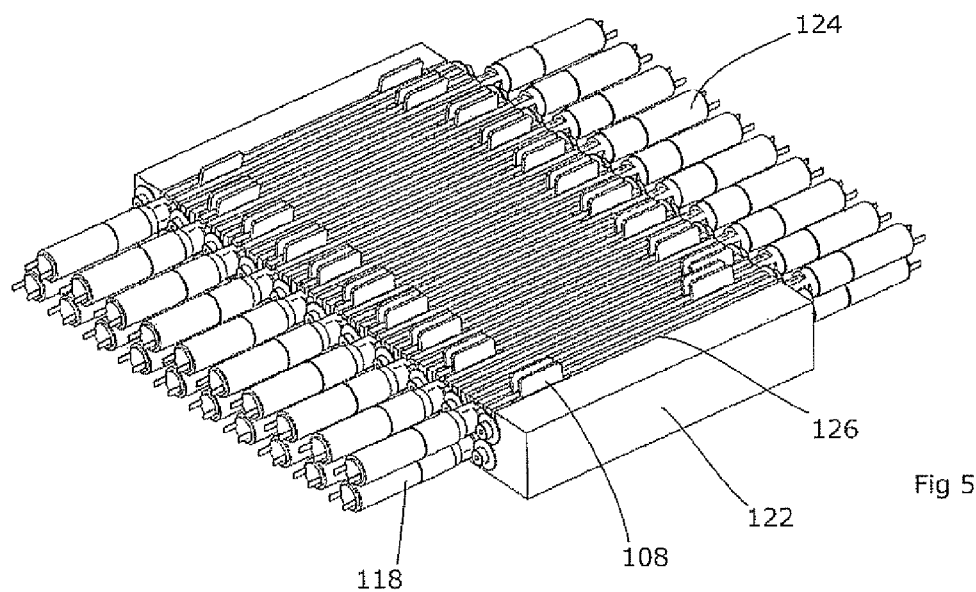
FIG. 5 shows a bank of leaf drives according to the present invention.

FIG. 5 shows one subframe, with the leaf bank and leaf guide removed. An array of motors 118 can be seen at one end, distant from the beam, and an opposing array of motors 124 can be seen at the other end, closest to the beam. The lugs 108 can be seen projecting from the guide slots 126; when this sub-assembly is replaced under (or over) the leaf array then these lugs will project into the recesses 106 of the drive portions 104 of the leaves 100. In this way, the drive mechanism can be easily removed for service, repair or replacement.

Figure 6:
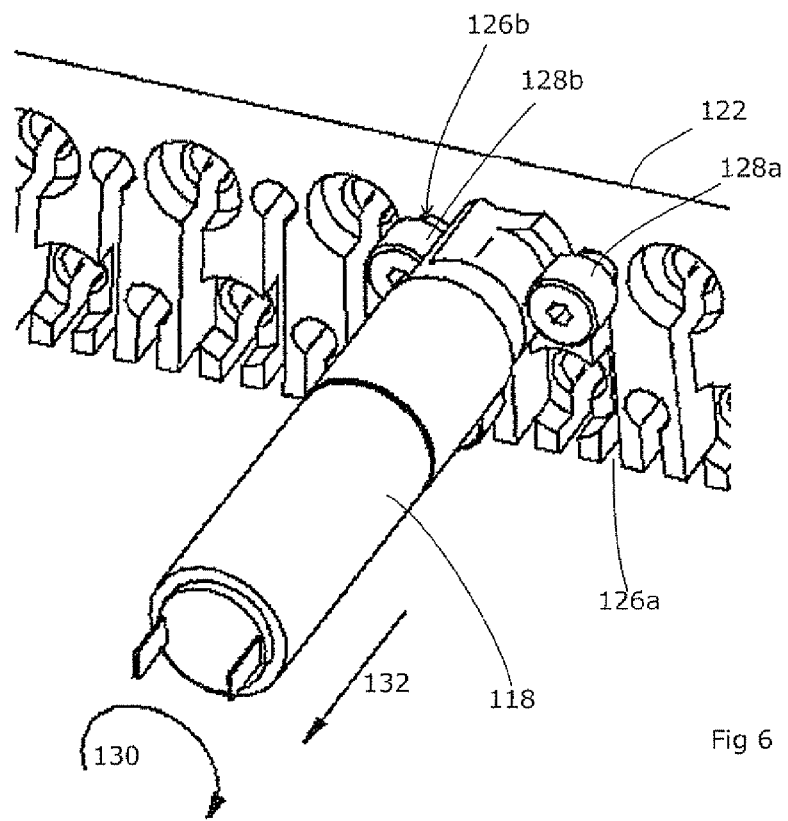
FIG. 6 shows the retention and removal of a single drive motor of the bank.

FIG. 6 shows how the motors 118 are retained on the subframe 122. Each motor has a pair of flanges projecting outwardly in two opposed directions around a part (but not all) of the circumference of the motor 118. Fortuitously, there will be a pair of guide slots 126a and 126b either side of the motor 118 which contain a leadscrew that is driven from the other end of the subframe 122. Thus, the ends (at least) of these slots 126a and 126b will be empty, and thus a mushroom-head screw 128a and 128b respectively can be screwed into the end of these slots 126a and 126b by providing a suitable tapping in the ends of the slots. In this way, by rotating the motor 118 so that the flanges are located under the mushroom-headed screws, then tightening the screws, the motor 118 will be retained securely. To remove the motor 118, both screws can be loosened, and the motor rotated in the direction of arrow 130 to move the flanges clear of the screw heads and allow the motor to be withdrawn in the direction of arrow 132.

In this arrangement, each screw will retain two motors, one on either side. This still permits individual motors to be removed, since the motors either side will still be retained by one screw, on their other side. This is generally preferable to providing each motor with a single flange and a single retaining screw; whilst this could be done, and would mean that each screw only held one motor, it would weaken the retention of the motors generally.

There could of course be further layers of leadscrews and motors beyond the two illustrated. Although this will incur a cost in terms of a greater complexity, it will permit a still greater ratio of motor spacing to leaf thickness to be achieved.

Figure 7:
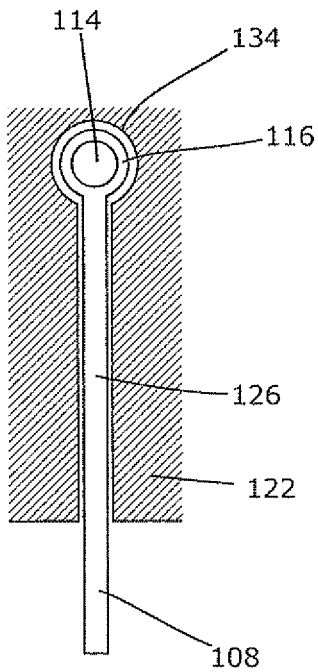
FIGS. 7 to 10 illustrate different profiles for the lug and the associated guide slot.

FIGS. 7 to 10 show alternative profiles for the lug and 108 and the guide slot 126 in which it slides. FIG. 7 shows the simplest option, a parallel-sided guide slot 126 formed in the subframe 122, with an enlarged root 134. The leadscrew 114 sits in the enlarged root 134 and is surrounded by the leadscrew nut 116. The lug 108 extends from the leadscrew nut 116, along the guide slot 126 and out of the subframe 122, to engage with the drive portion 104 of the leaf 100. This arrangement is obviously easiest to manufacture. However, it then requires the lug 108 to support the leaf 100 despite the fact that the centre of mass of the leaf 100 is offset from the line along which the lug 108 is driven. This will create a rotational moment on the lug 108 which will seek to rotate the lug 108 within the plane of the guide slot 126. This will create an uneven wear pattern on the lug 108, the leadscrew nut 116, and the leadscrew 114 and may be detrimental to the long-term performance of the drive mechanism.

Figure 8:
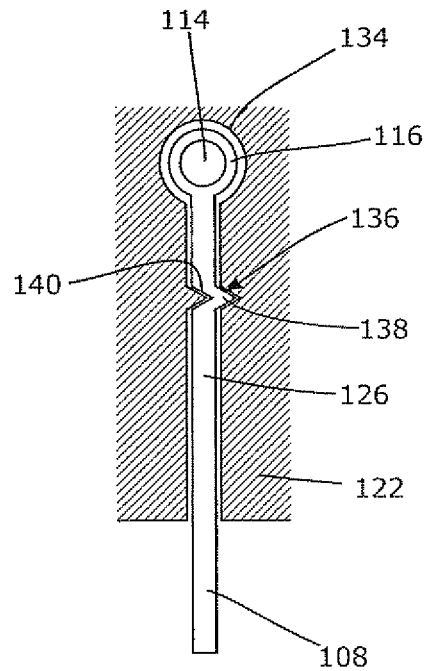

FIG. 8 therefore shows an adjustment to this design to alleviate this. The lug 108 is no longer parallel-sided, but includes a step 136 to one side part way along its length. The thickness of the lug 108 remains the same through the step; that is, the outward bulge 138 on one side is matched by a corresponding recess 140 on the other side. Matching formations are provided in the guide slot 126, to accommodate the outward bulge and to project into the recess.

By providing a non-flat surface to the lug 108 and a corresponding shape to the guide slot 126, rotation of the lug 108 in the guide slot 126 is inhibited. Support for the lug 108 against rotation is provided by the interaction of the bulge 138 and the recess 140 with the corresponding formations in the guide slot 126. Some lubrication may be useful in these areas, and a coating of graphite is suitable.

The arrangement shown in FIG. 8 is a simple and straightforward one which illustrates the concept. In practice, the bulges and recesses could be located elsewhere along the height of the lug 108/guide slot 126, and/or they could be duplicated so that multiple such formations are present. Where several such formations are provided, they could be oriented in the same direction, or in different orientations such as alternate directions or a mix of directions.

Figure 9:
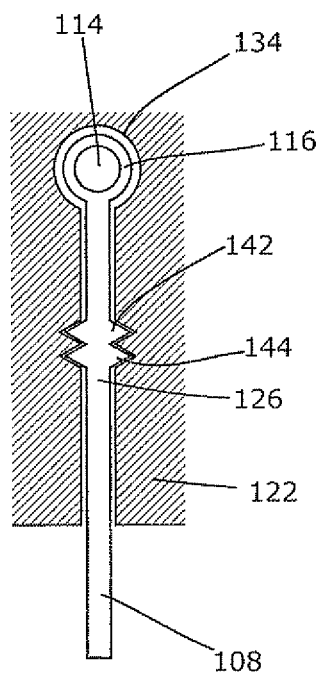

FIG. 9 shows a further variation. In this arrangement, the lug 108 has a pair of adjacent bulges 142, 144 on one side, duplicated on the other side. Corresponding recesses are formed in the guide slot 126. This arrangement has the advantage of being symmetrical as compared to that of FIG. 8, and also avoids any narrowing of the lug 108 that might cause it to be weakened.

Figure 10:
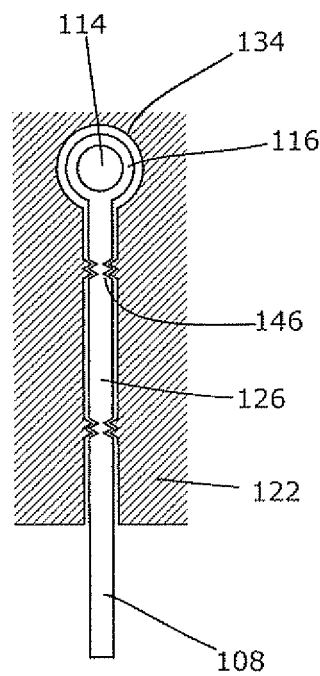

FIG. 10 shows a further alternative. A pattern of recesses 146 are formed in the sides of the lug 108, in this case four on each side in two groups of two each. Corresponding bulges are provided on the internal surfaces of the guide slot 126.

The shapes described above can be formed at the necessary scale by processes such as wire discharge machining.

FIG. 11 illustrates an alternative embodiment which may be simpler to manufacture in that the potentially complex shapes illustrated in FIGS. 7 to 10 are avoided.

In the above embodiments, the leafbank comprises a set of leaves that run in a leafguide, driven via separately attached drive couplings in the form of 'tails' that can be made of a lighter and cheaper material. A separate drive module uses guided 'keys' running in accurately machined slots, which fit into slots in the drive couplings. This allows the drive module to be removed and replaced very quickly. In the alternative embodiment, the keys are made with slots that fit over the edges of the slots in the drive couplings. It is therefore no longer necessary to constrain the keys against movement in their roll axis (around the axis of the leadscrew). This allows the drive couplings to be fitted with a looser tolerance, reducing manufacturing time and cost. This also allows the key drive profile to be greatly simplified.

With the key restrained in roll, it is possible to use the leadscrew to constrain the key in pitch and yaw, eliminating the need for the sliding contact and complicated machining of the drive module. The key can be simplified in material and form, reducing cost further.

Thus, referring to FIG. 11, a plurality of leaves 200 are provided in the usual side-by-side relationship. FIG. 11 shows a single leaf for clarity purposes, but this will be supplemented by many other leaves on either side—typically making up a bank of 20, 40 or 80 leaves in total on each bank. The leaves 200 are supported in a guide 202 which supports the upper edge 204 and the lower edge 206 of the leaves in slots 208 formed in the guide. The guide 202 can be fixed to one side of the radiotherapy beam so that the leaves 200 are extendable into the beam by sliding in the guide slots 208, thereby limiting the lateral extent of beam on that side to a desired shape. Alternatively, the guide 202 can be mounted on a moveable support, its position thereby being adjustable in rotation around the beam and/or longitudinally relative to the leaves so as to enable a wider range of adjustment of the leaf positions. A similar bank of leaves is usually provided on the opposite side of the beam in order to collimate the other lateral extent of the beam.

The leaf 200 is illustrated in FIG. 11 in a partially advanced position, shown in solid lines, and a withdrawn position shown in dotted lines. The withdrawn position illustrated is one that lies beyond the normal fully retracted position, in which the leaf has been fully retracted and then withdrawn further so that is no longer supported by the guide slots 208. Such a position would only be reached during assembly, maintenance, or disassembly, but allows us to illustrate the construction of the leaf.

Each leaf 210 is of a substantially radio-opaque material such as tungsten, and the drive couplings 212 can be of a lighter and less expensive material such as steel or aluminium. This allows the tungsten forward portion 210 to be projected into the beam, driven by a rearward drive coupling that never enters the beam and does not therefore need to be of a radiopaque material. The overall weight and cost of the unit is thereby minimised.

The drive coupling 212 of each leaf 200 includes a rectangular cut-out section 214, visible more clearly in the dotted outline version of the leaf 200 shown in the withdrawn position. This receives a corresponding drive lug 216 that is threaded onto a leadscrew 218. The leadscrew 218 is, in turn, mounted in a subframe 220 and provided with a drive motor (not shown) in a pattern similar to that described above.

In this embodiment, the leadscrew 218 is supported by the subframe 220 at either end. The drive lug 216 has an extent in the longitudinal direction (i.e. parallel to the leadscrew 218 and the leaf 200) of (for example) 10 mm or more, generally at least 50% of its extent transverse to the leadscrew 218. It is therefore constrained against rotation about axes transverse to the leadscrew 218.

The drive lug 216 extends transversely away from the leadscrew 218 toward the cut-out 214 of the leaf tail 212. The lug 216 ends with an interface region that keys with the cut-out 214; in this example it comprises a solid rectangular section 222 that matches the rectangular cut-out 214 and (when assembled) fits into the cut-out 214. On either longitudinal side of the rectangular section 222, there are laterally-spaced flanges 224 that fit snugly either side of the leaf tail 212 and prevent the lug 216 from rotating around the leadscrew 218.

Thus, the drive lug 216 is prevented from movement in all axes other that longitudinal translation along the leadscrew 218 as the leadscrew 218 rotates. This movement of the drive lug 216 will then cause a corresponding movement of the leaf 200.

Through the use of the above-described embodiments, it is possible to produce a reliable 160-leaf multi-leaf collimator, that is a collimator with 80 leaves on each side of the beam. Current commercially-available large-aperture MLCs have a total of 80 leaves, i.e. 40 leaves per side as illustrated in FIG. 4, but the increased space efficiency achieved by the present invention allows this to be doubled by appropriate thinning of the leaves. This means that instead of a projected width at the isocentre of 1 cm, each such leaf will have a resolution of 5 mm—with an attendant improvement in resolution and accuracy of delivery.

An improvement of the resolution to 160 leaves instead of 80 will also require improvements in the treatment planning systems and software, and the associated control systems and software in order to take advantage of the additional degrees of freedom offered by doubling the number of leaves. In the longer term, this does not present a particular difficulty, but in the short term clinics may wish to replace hardware and other systems incrementally. Accordingly, there may be advantages in an MLC that retains the ability to operate in a 160-leaf mode but which is fully compatible with 80-leaf control systems.

This is indeed possible through the present invention. If the same leaves are inserted into the same leaf guide, but oriented so that they are organised in identical pairs, then these leaf pairs can be driven together, in unison, by providing suitable upper and lower subframes 120 as illustrated in FIG. 3 et seq. Adjacent leaf pairs will have co-located recesses 106 in their associated drive couplings, into both of which the same lug 108 can project. Some care may need to be taken in designing the appropriate width for the lug 108 to ensure that an adequate drive is transmitted to both leaves.

Thus, the device will operate as an 80-leaf collimator and can be controlled and driven in the same way. However, as and when the clinic is able to upgrade other aspects of their radiotherapy equipment, the upper and lower subframes can be replaced with items adapted for 160-leaf operation and the leaves removed and re-inserted in the pattern appropriate to independent operation of each leaf.

Another use of the described collimator drive is for a variable-pitch collimator. Such a collimator includes leaves having a plurality of different thicknesses, such as a group of narrow leaves in the central region flanked on either side by relatively thicker leaves. Thus, a fine resolution is available in the central area of the aperture where it is usually needed, but the full aperture of the MLC is available when needed. Such collimators are limited by (inter alia) difficulty in driving the various leaves accurately and the present invention can assist with this.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:

1. A multi-leaf collimator for a radiotherapy apparatus, comprising at least one array of elongate leaves spaced in a lateral direction and a plurality of motors, each leaf being driven by one of the motors of the plurality of motors, each motor connected to one of the leaves via a drive means so as to extend or retract the leaf in a longitudinal direction, the multi-leaf collimator comprising a sub-frame on which at least a subset of the plurality of motors are mounted, the sub-frame being mounted at a location spaced from the leaf array in a direction transverse to the lateral and longitudinal directions, the drive means including a plurality of elongate threaded drives which are disposed longitudinally, each elongate threaded drive being driven by one of the motors of the subset of motors and being operatively connected to a leaf thereby to drive that leaf, wherein some of the subset of the plurality of motors mounted on the sub-frame are mounted at a first longitudinal end of the elongate threaded drives, and a remainder of the subset of the plurality of motors are mounted at a second longitudinal end of the elongate threaded drives.

2. The multi-leaf collimator according to claim 1 in which the elongate threaded drives are neighboured on either lateral side by a first elongate threaded drive driven by one of the motors mounted at the same longitudinal end and a second elongate threaded drive driven by one of the motors mounted at the opposite longitudinal end.

3. The multi-leaf collimator according to claim 1 in which the elongate threaded drives are mounted in the subframe at one of a plurality of spacings from the at least one array of elongate leaves.

4. The multi-leaf collimator according to claim 1 in which the elongate threaded drives are mounted in the subframe at one of two spacings from the at least one array of elongate leaves, laterally neighbouring elongate threaded drives being mounted at alternating spacings.

5. The multi-leaf collimator according to claim 1 in which the elongate threaded drives are mounted within a bore in the subframe.

6. The multi-leaf collimator according to claim 1, wherein the subframe is an upper subframe and further comprising a lower subframe, the lower subframe being mounted at a location spaced from the leaf array in an opposite direction to that of the upper subframe and on which a remainder of the plurality of motors are mounted.

7. The multi-leaf collimator according to claim 6 in which the plurality of the motors mounted on the lower subframe are mounted at a first longitudinal end of the elongate threaded drives and a remainder are mounted at a second, opposing, longitudinal end of the elongate threaded drives.

8. The multi-leaf collimator according to claim 7 in which the elongate threaded drives are neighboured on either lateral side by a first elongate threaded drive driven by one of the motors mounted at the same longitudinal end and a second elongate threaded drive driven by one of the motors mounted at the opposite longitudinal end.

9. The multi-leaf collimator according to claim 5 in which the elongate threaded drives are mounted in the subframe at one of two spacings from the leaf, laterally neighbouring threaded drives being mounted at alternating spacings.

10. The multi-leaf collimator according to claim 6 in which the elongate threaded drives are mounted within a bore in the lower subframe.

11. The multi-leaf collimator according to claim 1 in which the elongate threaded drives are leadscrews.

12. The multi-leaf collimator according to claim 6 in which half of the leaves are driven via the upper subframe and half are driven via the lower subframe.

13. The multi-leaf collimator according to claim 6 in which adjacent leaves in the array are driven alternately via the upper subframe and via the lower subframe.

14. The multi-leaf collimator according to claim 1 in which the leaves are mounted in a machined guide thereby to allow longitudinal motion.

15. The multi-leaf collimator according to claim 14 in which the subframe is mounted on the machined guide.

16. The multi-leaf collimator according to claim 1 in which the leaves are of a first material that is substantially radio-opaque and including a drive coupling attached to the rear of each leaf via which the leaves are driven, the drive coupling being of a second material.

17. The multi-leaf collimator according to claim 16 in which the drive couplings are driven from an elongate edge thereof.

18. The multi-leaf collimator according to claim 1 in which the drive means further includes a threaded member on the threaded drives.

19. The multi-leaf collimator according to claim 18 in which an operative connection between the threaded member and the leaf acts to restrain rotation of the threaded member about the threaded drive.

20. The multi-leaf collimator according to claim 18 in which the threaded member urges a projecting lug.

21. The multi-leaf collimator according to claim 20, in which the leaves are of a first material that is substantially radio-opaque and including a drive coupling attached to the rear of each leaf via which the leaves are driven, the drive coupling being of a second material, and in which the projecting lug engages with a recess on the drive coupling.

22. The multi-leaf collimator according to claim 20 in which the lug includes spaced flanges positioned to lie adjacent a leaf edge.

23. The multi-leaf collimator according to claim 20 in which the lug has a length in a direction parallel to the threaded member that is at least 50% of a length of the lug transverse to the threaded member.

24. The multi-leaf collimator according to claim 20 in which the lug is held in machined slot in the subframe.

25. The multi-leaf collimator according to claim 24 in which the machined slot has non-parallel sides.

26. The multi-leaf collimator according to claim 1 in which the leaves are arranged in groups, each leaf of a group being identically oriented and driven in unison by the same drive means.

27. The multi-leaf collimator according to claim 26 in which each group consists of two leaves.

28. A multi-leaf collimator for a radiotherapy apparatus, comprising at least one array of elongate leaves spaced in a lateral direction and a plurality of motors, each leaf being driven by one of the motors of the plurality of motors, the plurality of motors being connected to the plurality of elongate leaves via a drive means so as to extend or retract the leaves in a longitudinal direction, the multi-leaf collimator further comprising:
   an upper sub-frame on which at least a first subset of the plurality of motors are mounted, the upper sub-frame being mounted at a location spaced from the leaf array in a direction transverse to the lateral and longitudinal directions; and
   a lower sub-frame on which at least a second subset of the plurality of motors are mounted, the lower sub-frame mounted at a location spaced from the leaf array in an opposite direction to that of the upper sub-frame;
   the drive means comprising a plurality of elongate threaded drives which are disposed longitudinally, each elongate threaded drive being driven by one of the motors of the plurality of motors and being operatively connected to a leaf thereby to drive that leaf.

* * * * *